(12) United States Patent
Wright

(10) Patent No.: US 6,737,274 B1
(45) Date of Patent: May 18, 2004

(54) COMPARATOR FOR TIME-TEMPERATURE INDICATOR

(75) Inventor: Bruce Butler Wright, Natick, MA (US)

(73) Assignee: United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/244,961

(22) Filed: Feb. 4, 1999

(51) Int. Cl.⁷ .............................................. G01N 33/02
(52) U.S. Cl. ................................. 436/1; 436/2; 436/164; 422/61; 73/61.46; 73/61.76; 426/88; 434/283
(58) Field of Search ................................ 436/1–2, 164; 422/56, 58, 61; 73/61.46, 61.76; 434/84, 283; 426/87–88

(56) References Cited

U.S. PATENT DOCUMENTS

| | | | |
|---|---|---|---|
| 3,344,670 A | * | 10/1967 | Olsen et al. .................. 73/356 |
| 3,942,467 A | | 3/1976 | Witonsky |
| 3,965,741 A | | 6/1976 | Wachtell |
| 4,042,336 A | | 8/1977 | Larsson |
| 4,151,748 A | | 5/1979 | Baum |
| 4,195,058 A | | 3/1980 | Patel |
| 4,292,916 A | | 10/1981 | Bradley |
| 4,339,207 A | | 7/1982 | Hof et al. |
| 4,382,700 A | | 5/1983 | Youngren |
| 4,389,217 A | * | 6/1983 | Baughman et al. ............ 436/2 |
| 4,432,656 A | | 2/1984 | Allmendinger |
| 4,533,640 A | | 8/1985 | Shafer |
| 4,804,275 A | | 2/1989 | Kang |
| 4,892,677 A | | 1/1990 | Preziosi |
| 5,045,283 A | | 9/1991 | Patel |
| 5,057,434 A | | 10/1991 | Prusik |
| 5,168,042 A | * | 12/1992 | Ly ............................... 422/56 |

OTHER PUBLICATIONS

Article entitled "Time–Temperature Indicators," from periodical *Food Technology*, Oct. 1991, pp. 70–80, by Taoukis, Fu and Labuza.

* cited by examiner

Primary Examiner—Lyle A. Alexander
(74) Attorney, Agent, or Firm—Vincent J. Ranucci

(57) ABSTRACT

A comparator for use with a time-temperature indicator wherein the time-temperature indicator includes an active portion having an initial color and which undergoes chemical changes as time elapses and at a rate related to the temperature of the surrounding environment and wherein the chemical changes produce changes in the color of the active portion. The comparator comprises a substantially planar support member, and a plurality of comparator stages located on the support member. Each comparator stage comprises a first portion having a reference color and a second portion having a predetermined color that is the same as one of the colors to which the active portion of the time-temperature indicator changes. The predetermined colors of the second portions of the comparator stages darken in a progressive manner such that the predetermined color of the second portion of a first one of the comparator stages is substantially lighter than the reference color of the first stage and the predetermined color of the second portion of a last one of the comparator stages is substantially darker than the reference color of the last comparator stage. A user of the comparator compares the color of the active portion of the time-temperature indicator to each comparator stage to determine if the color of the active portion is the same as the predetermined color of the second portion of any of the comparator stages.

2 Claims, 1 Drawing Sheet

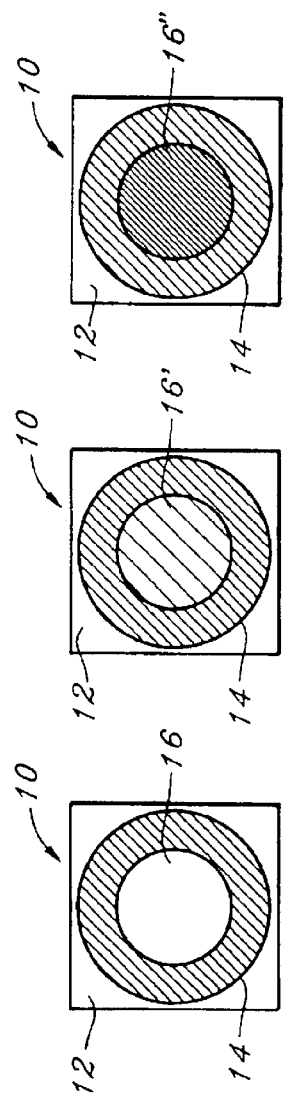
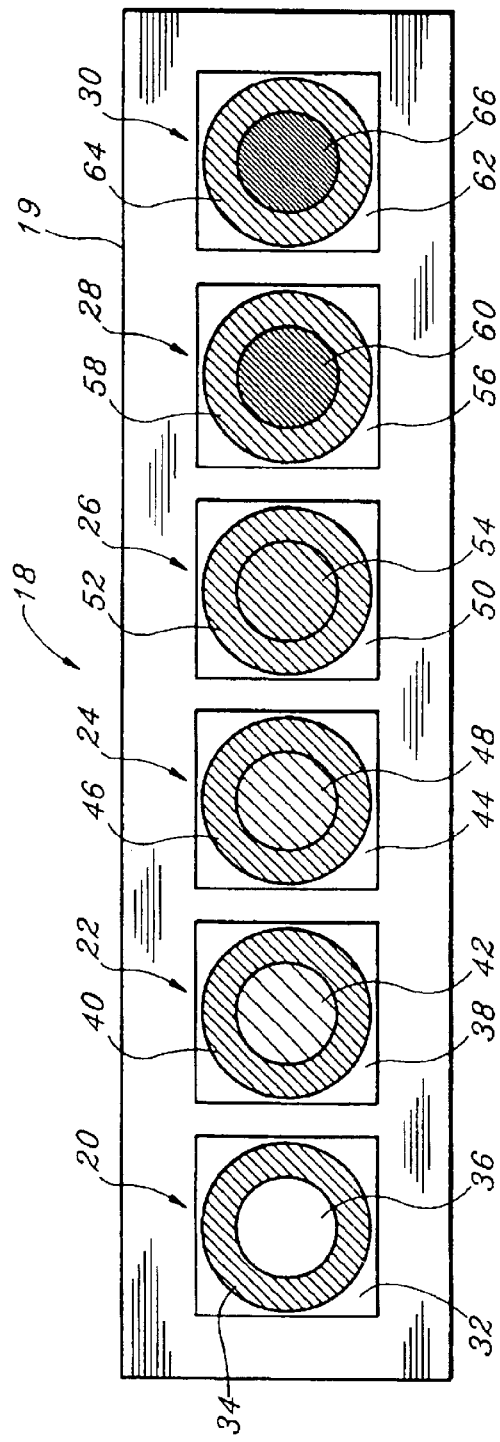

COMPARATOR FOR TIME-TEMPERATURE INDICATOR

BACKGROUND OF THE INVENTION

The invention described herein may be manufactured, used and licensed by or for the Government for Governmental purposes without the payment to us of any royalty thereon.

1. Field of the Invention

The present invention generally relates to a comparator for use in interpreting data provided by a time-temperature indicator.

2. Problem to be Solved

Time-temperature indicators ("TTIs") are used for external monitoring of the time-temperature history of various products such as food. Typically, This are used to monitor the condition of military-type rations. One such ration is typically referred to as Meal-Ready-To-Eat ("MRE"). The quality of MRE rations is highly dependent upon the time the MREs spend in storage and the storage temperature.

There are many styles and configurations of TTIs. TTIs are generally described in the periodical entitled *Food Technology*, October 1991, pages 72–75. TTIs are also generally described in U.S. Pat. Nos. 5,045,283 and 5,057,434. One type of TTI is referred to as the "bull's eye" style TTI and is configured as a label. The label has an adhesive backing that is adhered to a ration container. The label has a circular-shaped, outer reference portion and a circular-shaped, active portion within the reference portion. The reference and active portions are concentrically arranged. In another type of "bull's eye" style TTI, the reference portion is within the active portion.

The active portion of the "bull's eye" style TTI changes color over time wherein the rate of change is dependent upon the temperature to which the TTI is exposed. Specifically, the rate of darkening of the active portion is dependent upon the storage temperature. Since the quality of the MREs is highly dependent upon the time spent in storage and the storage temperature, the darkening of the active portion can be related to the expiration of the shelf life of the MREs, i.e. degradation in quality of the MREs. The "bull's eye" type TTIs can be configured to have a predetermined target shelf life. Initially, the color of the active portion matches the color of the peripheral or base portion. The target shelf life is attained when the color of the active portion matches the color of the reference portion. One commercially available "bull's eye" type TTIs is based on a target shelf life of three (3) years at 80° F. Thus, if the "bull's eye" type TTI is applied to rations that are stored at a temperature of 80° F., the time it takes for the color of the active portion to match the color of the reference portion will be about three (3) years. However, if the storage temperature is greater than 80° F., the time it takes for the color of the active portion to match the color of the reference portion will be less than three (3) years. Therefore, the quality of the MRE will be comparable to that of a MRE that was in storage for three (3) years even though it was actually in storage less than three (3) years. On the other hand, storing the rations at temperatures below 80° F. increases the time required for the color of the active portion of the TTI to match the color of the reference portion. Thus, the shelf life of the ration is extended beyond three years.

Typically, instrumentation is used to evaluate the change in color of the active portion of the TTI in order to accurately determine the time-temperature condition of the ration to which the TTI is attached. One such instrument is a densitometer. This instrument measures the optical density of both the active portion and the reference portion or the base portion of the "bull's eye" type TTI. However, such instrumentation is expensive. Furthermore, such instrumentation is bulky and inconvenient to carry to the site of the stored rations. What is needed is a lightweight, inexpensive and simple-to-use apparatus for evaluating the color change of the active portion of a TTI label in order to determine the condition of the ration, and hence, the quality of the ration.

It is therefore an object of the present invention to provide an apparatus for evaluating the color change of an active portion of a TTI wherein the apparatus is inexpensive to manufacture.

It is another object of the present invention to provide an apparatus for evaluating the color change of an active portion of a TTI wherein the apparatus is lightweight.

It is a further object of the present invention to provide an apparatus for evaluating the color change of an active portion of a TTI wherein the apparatus is easy to use.

It is yet another object of the present invention to provide an apparatus for evaluating the color change of an active portion of a TTI wherein the apparatus can be conveniently stored when not in use.

Other objects and advantages of the present invention will be apparent to one of ordinary skill in the art in light of the ensuing description of the present invention.

SUMMARY OF THE INVENTION

The present invention is directed to a comparator for use with a time-temperature indicator that has an active portion which has an initial color and which undergoes chemical changes as time elapses. The rate of chemical change is dependent upon the temperature of the surrounding environment. The chemical changes produce visual changes in the color of the active portion of the time-temperature indicator. The comparator comprises a support member, and a plurality of comparator stages located on the support member. Each comparator stage comprises a first portion that has a reference color and a second portion that has a predetermined color that is the same as one of the colors to which the active portion of the time-temperature indicator changes as time elapses. The colors of the second portions of the comparator stages darken in a progressive manner such that the predetermined color of the second portion of a first one of the comparator stages is substantially lighter than the reference color of the first stage and the predetermined color of the second portion of a last one of the comparator stages is substantially darker than the reference color of the last comparator stage.

The number of TTI comparator stages may be varied depending on the requirements. In one embodiment, each stage is assigned indicia such as a number. For example, the initial stage can be designated by the number zero (0). Succeeding stages may be designated with consecutive positive integers. Other identification systems can also be used with the comparator stages, e.g. combinations of letters and numbers.

A user of the comparator of the present invention compares the color of the active portion of a TTI that is attached to a ration or food container (or pouch or other packaging) to the predetermined color of the second portion of each stage of the TTI comparator. The user then selects the comparator stage that has a second portion that has a predetermined color that matches the color of the active portion of the TTI label. If the shade of the color of the active portion of the TTI label is between the shades of the colors of the second portions of adjacent comparator stages, then the user selects the comparator stage that has the second portion with the lighter shade of color. The user then correlates the indicia of the selected Tm comparator stage to a particular condition of the ration.

The TTI comparator of the present invention has numerous advantages in comparison to conventional devices. For example, the TTI comparator of the present invention is relatively simple and inexpensive to manufacture in comparison to instruments such as densitometers. Furthermore, the TTI comparator of the present invention is easy to transport and may be conveniently and easily stored when not in use.

BRIEF DESCRIPTION OF THE DRAWINGS

The features of the invention are believed to be novel and the elements characteristic of the invention are set forth with-particularity in the appended claims. The figures are for illustration purposes only and are not drawn to scale. The invention itself, however, both as to organization and method of operation, may best be understood by reference to the detailed description which follows taken in conjunction with the accompanying drawings in which:

FIGS. 1–3 illustrates a "bull's eye" type TTI wherein an active portion of the TTI is undergoing changes in color.

FIG. 4 is a plan view of the TTI comparator of the present invention.

DETAILED DESCRIPTION OF THE INVENTION

In describing the preferred embodiments of the present invention, reference will be made herein to FIGS. 1–4 of the drawings in which like numerals refer to like features of the invention.

Although the ensuing description is in terms of how the comparator of the present invention is used with the TTI having the configuration shown in FIGS. 1–3, it is to be understood that the comparator of the present invention, shown in FIG. 4, may be used with TTIs having other types of configurations.

FIG. 1 shows time-temperature indicator ("TTI") 10 which has a "bull's eye" configuration. TTI 10 is configured as a label that can be attached to food or ration containers. TTI 10 comprises a base region 12, a reference portion 14 and an active portion 16. Reference portion 14 and active portion 16 are circular in shape and are concentrically arranged as shown in FIG. 1. Base region 12 has a fixed color. Reference portion 14 has a fixed color which is substantially darker in shade than the color of base region 12. The active portion 16 initially has a color that is the same as base region 12. In one type of TTI, active portion 16 is comprised of a monomer. As the monomer polymerizes, it darkens as time elapses and darkens more rapidly as the temperature increases. A red-colored film is typically disposed over TTI 10 to block ultraviolet (UV) light.

FIG. 1 shows active portion 16 having an initial color that is the same as that of base region 12. As time elapses, the color of active portion 16 darkens. This is represented by active portion 16' shown in FIG. 2 wherein the shade of the color of active portion 16' is lighter than that of reference portion 14. FIG. 3 shows TTI 10 wherein the color of the active portion has further darkened. As shown in FIG. 3, the shade of the color of the active portion is darker than the reference portion 14. This condition is represented by active portion 16".

FIG. 4 shows the TTI comparator 18 of the present invention. Comparator 18 comprises support member 19 and a plurality of comparator stages 20, 22, 24, 26, 28 and 30 attached to the support member 19. Although the ensuing description is in terms of comparator 18 having six (6) stages, it is to be understood that the comparator 18 may utilize less than or more than six (6) stages. In one embodiment, each comparator stage 20, 22, 24, 26, 28 and 30 may be realized as a label having an adhesive backing that is applied to support member 19. In another embodiment, each comparator stage is printed on support member 19. In a preferred embodiment, support member 19 is substantially flat and is fabricated from lightweight materials such as paper, cardboard, plastic, wood, etc. Other suitable materials may also be used.

Referring to FIG. 4, stage 20 comprises base portion 32, reference portion 34 and test portion 36. Stage 22 comprises base portion 38, reference portion 40 and test portion 42.

Stage 24 comprises base portion 44, reference portion 46 and test portion 48. Stage 26 comprises base portion 50, reference portion 52 and test portion 54. Stage 28 comprises base portion 56, reference portion 58 and test portion 60. Stage 30 comprises base portion 62, reference portion 64 and test portion 66. As shown in FIG. 4, the shade of the color of the test portions 36, 42, 48, 54, 60 and 66 darken progressively from left to right. As a result of such a configuration, each test portion has a predetermined color that is the same as one of the colors to which active portion 16 of TTI 10 changes as time elapses, changing more rapidly with an increase in temperature. The color of each reference portion of each comparator does not change and therefore functions as a reference.

Referring to FIG. 4, the reference and test portions may be arranged, with respect to another, in any one of a variety of arrangements and may be configured to have any type of geometric shapes, e.g. square, rectangular, triangular, etc. For example, as shown in FIG. 4, the reference and test portions of the stages are shown to be substantially circular in shape and concentrically arranged wherein the diameter of the reference portion is greater than the diameter of the test portion. However, FIG. 4 illustrates just one example and it is to be understood that other configurations may be implemented. For example, the reference and test portions may be configured such that the reference and test portions are substantially circular in shape and are concentrically arranged with the reference portion being located within the perimeter of the test portion. In another example, the reference and test portions may be realized by strips adjacent to one another. As previously stated, many other configurations are possible. Similarly, although the base region of each comparison stage is shown in FIG. 4 to have a square shape, each base region may be configured to have other shapes. Furthermore, each comparator stage may be configured without a base region.

Each comparator stage has indicia (not shown) associated therewith to enable the user to identify a particular stage. The indicia of each stage is assigned a particular time-temperature condition, e.g. excellent, good, poor, etc. This will be explained in detail later.

Referring to FIG. 4, in a preferred embodiment, the color of the base region of each stage 20, 22, 24, 26, 28 and 30 is substantially the same as base region 12 of TTI 10, and the reference portion of each stage 20, 22, 24, 26, 28 and 30 is substantially the same as that of reference portion 14 of TTI 10. It is also highly preferable that the color of test portion 36 of stage 20 (which is the first stage) is substantially the same as the color of the initial color of active portion 16 of TTI 10. The initial color of the active portion 16 is the color of portion 16 when first applied to the ration at the beginning of its shelf life.

Referring to FIGS. 1–4, in order to determine the time-temperature condition of a ration or food product, the user holds support member 19 adjacent to TTI 10 and compares the color of active portion 16 TTI 10 to the predetermined color of the test portion of each stage 20, 22, 24, 26, 28 and 30. The user then selects the comparator stage that has the test portion having the color that matches the color of active portion 16. If the shade of the color of active portion 16 is between the shades of the colors of the test portions of two adjacent comparator stages, the user selects the comparator stage having the test portion with the lighter shade of color. The user then correlates the indicia of the selected comparator stage to a particular time-temperature condition. In one embodiment, this can be accomplished by a using a chart or "look-up" table that contains the indicia of each comparator stage and the corresponding time-temperature condition. In another embodiment, the user inputs the indicia of the selected comparator stage into a microprocessor, personal computer or laptop (hereinafter collectively referred to as "computer"). The computer comprises a memory having stored therein a chart, table or array containing the indicia of all the comparator stages and the corresponding time-temperature conditions. Upon entry of the indicia of the selected comparator stage, the computer outputs the corresponding time-temperature condition. The hand-held chart or table, described above, or the computer, may be configured to also provide additional information or instructions as to what steps should be taken regarding the rations, e.g. consume immediately, dispose, maintain in storage, etc.

Another advantage of comparator 18 of the present invention is that the time-temperature condition of the ration may also be determined when the shade of the color of the active portion of the TTI 10 falls between the shades of the colors of the test portions of two adjacent comparator stages. As described above, if such a condition does occur, the user selects the comparator stage having the test portion with the lighter shade of color. Furthermore, if the color of the active portion of the TTI is darker than the color of the test portion 66 of last comparator stage 30 (see FIG. 4), then the user selects stage 30 and uses the indicia associated with that stage to determine the time-temperature condition of the ration. Thus, comparator 18 allows for the determination of time-temperature condition for at least twelve (12) different shades of color of the active portion of a TTI.

Table I further illustrates how comparator 18 of the present invention can be used to determine the time-temperature condition of rations. For purposes of explaining how comparator 18 is used to determine time-temperature conditions, comparator stages 20, 22, 24, 26, 28 and 30 have been assigned numerical indicia 0–5, respectively, wherein "0" designates a first or initial comparator stage. As mentioned above, such indicia may be located adjacent the appropriate comparator stage. The information listed under the heading "Elapsed Time At 80° F." is based on a TTI that is configured to have a target shelf life of three (3) years at a temperature of 80° F. (Such a configuration has been previously discussed). It is to be understood that Table I may contain information relative to TTIs that are configured to have different target shelf lives at different temperatures. Furthermore, it is to be understood that the format of Table I and the information presented therein is for purposes of facilitating understanding of the invention and constitutes only one example. Other suitable formats may also be used.

TABLE I

| Selected Stage | Elapsed Time At 80° F. | Ration Quality |
| --- | --- | --- |
| 0 | 6 months | Excellent |
| 1 | 1 year | Excellent |
| 2 | 2 years | Good |
| 3 | 3 years | Good |
| 4 | 3 ½ years | Poor |
| 5 | 4 years | Very Poor |

Table I may be realized as a printed table that can be hand carried, or it may be stored in the memory of a computer. The following examples, taken in conjunction with FIGS. 1–4 and Table I, will further illustrate the workings and advantages of comparator 18 of the present invention.

EXAMPLE 1

It is desired to determine the quality of a ration having TTI 10 attached thereto. The active portion of TTI 10 has a color represented by active portion 16 shown in FIG. 1. The user compares the color of active portion 16 to the predetermined color of the test portion of each stage 20, 22, 24, 26, 28 and 30. The user determines that the color of the active portion 16 matches the color of the test portion 36 of stage 20. As described above, stage 20 has been assigned numerical indicia "0". The user then locates indicia "0" in Table I (or inputs "0" into the computer) under the heading "Selected Stage" and the corresponding information, e.g. Elapsed Time At 80° F. and Ration Quality, in the row corresponding to "0". As shown in Table I, the corresponding Elapsed Time At 80° F. is about six (6) months and the Ration Quality is excellent.

EXAMPLE 2

It is desired to determine the quality of a ration having TTI 10 attached thereto. The active portion of TTI 10 has a color represented by active portion 16' shown in FIG. 2. The user compares the color of active portion 16' to the color of the test portion of each stage 20, 22, 24, 26, 28 and 30. The user determines that the color of the active portion 16' matches the color of test portion 42 of stage 22. As described above, stage 22 has been assigned numerical indicia "1". The user then locates indicia "1" in Table I (or inputs "1" into the computer) under the heading "Selected Stage" and then observes the corresponding information, e.g. Elapsed Time At 80° F. and Ration Quality, in the row corresponding to "1". As shown in Table I, the corresponding Elapsed Time At 80° F. is one (1) year and the Ration Quality is excellent.

EXAMPLE 3

It is desired to determine the quality of a ration having TTI 10 attached thereto. The active portion of TTI 10 has a color represented by active portion 16" shown in FIG. 3. The user compares the color of active portion 16" to the color of the test portion of each stage 20, 22, 24, 26, 28 and 30. The user determines that the color of the active portion 16" matches the color of test portion 60 of stage 28. As described above, stage 28 has been assigned numerical indicia "4". The user then locates indicia "4" in Table I (or inputs "4" into the computer) under the heading "Selected Stage" and then observes the corresponding information, e.g. Elapsed Time At 80° F. and Ration Quality, in the row corresponding to "4". As shown in Table I, the corresponding Elapsed Time At 80° F. is three and one-half (3½) years and the Ration Quality is poor.

Thus, TTI comparator 18 of the present invention achieves the objects set forth above. Specifically, TTI comparator 18 is:

a) lightweight;

b) easy and convenient to transport;

c) easy to store when not in use;

d) easy to use; and e) inexpensive to manufacture.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A comparator for use with a time-temperature indicator, said indicator for external monitoring of a time-temperature exposure of a product, said exposure having an exposure reference of 80° F. over three years, whereby said exposure may vary such that as the temperature increases, the time decreases, and as the temperature decreases, the time increases, the time-temperature indicator having an active portion having an initial color which undergoes chemical changes as time elapses and at a rate related to the temperature of the surrounding environment wherein the chemical changes produce changes in the color of the active portion, the comparator having a predetermined color that is the cumulative equivalent to 80° F. over three years, the comparator comprising:

a supporting member;

a plurality of comparator stages located on the support member, each comparator stage comprising a first portion having a reference color and a second portion having a predetermined color that is the same as one of the colors to which the active portion of the time-temperature indicator changes, the colors of the second portions of the comparator stages darkening in a progressive manner such that the predetermined color of the second portion of a first one of the comparator stages is substantially lighter than the reference color of the first stage and the predetermined color of the second portion of a last one of the comparator stages is substantially darker than the reference color of the last comparator stage;

information describing a condition of said product at each comparator stage; indicia means located on the support member to facilitate identification of each stage, said indicia means corresponding to a condition of said product at a said stage as described by the information; and means for storing said information;

whereby a user of the comparator compares the color of the active portion of the time-temperature indicator to each comparator stage to determine if the color of the active portion is the same as the color of the second portion of any of the comparator stages; and whereby said user correlates the indicia of the stage, having the same color as said active portion, with said storing means for accessing information corresponding to the indicia for determining the condition of the product; said comparator for determining an amount of color that has developed in the time-temperature indicator, based on the exposure reference of 80° F. for three years as an appropriate shelf life of the product said product being for example a military ration, such exposure reference representing a point between binary conditions of the product, said first condition being prior to the point and being positive and said product being usable, and said second condition being after the point and being negative and said product having uncertain use by passing such point as a result of deterioration of the product;

said comparator being of a design having a hue and color saturation of the colors of the active potion of the time-temperature indicator, and for comparison of the colors, said comparison using a densitometer-like instrument for measurement of optical density of the color saturation.

2. A method of determining the time-temperature condition of a food product having applied thereto a time-temperature indicator, the indicator having an active portion having an initial color which undergoes chemical changes as time elapses and at a rate related to the temperature of the surrounding environment, said time and temperature having a reference of 80° F. over three years, whereby said time and temperature may vary such that as the temperature increases the time decreases, and as the temperature decreases, the time increases, wherein the chemical changes produces changes in color of the active portion, the method comprising the steps of:

(a) providing a comparator having a predetermined color that is the cumulative equivalent to 80° F. over three years, the comparator comprising support member, and a plurality of comparator stages located on the support member, each comparator stage comprising a first portion having a reference color and a second portion having a predetermined color that is the same as one of the colors to which the active portion of the time-temperature indicator changes, the colors of the second portions of the comparator stages darkening in a progressive manner such that the predetermined color of the second portion of a first one of the comparator stages is substantially lighter than the reference color of the first stage and the predetermined color of the second portion of a last one of the comparator stages is substantially darker than the reference portion of the last comparator stage;

(b) comparing the color of the active portion of the time-temperature indicator to the predetermined color of the second portion of each comparator stage;

(c) selecting the comparator stage having the second portion with the predetermined color that matches the color of the active portion of the time-temperature indicator;

(d) storing information describing a condition of the product, each condition being identified by an indicia identifying the condition of the product at a particular stage;

(e) correlating the indicia of the selected comparator stage to a particular condition of the product; and (f) retrieving said stored information describing the condition of the product at the selected comparator stage, said comparator for determining an amount of color that has developed in the time-temperature indicator, based on the exposure reference of 80° F. for three years as an appropriate shelf life of the product, said product being for example a military ration, such exposure reference representing a point between binary conditions of the product, said first condition being prior to the point and being positive and said product being usable, and said second condition being after the point and being negative and said product having uncertain use by passing such point as a result of deterioration of the product; said comparator being of a design having a hue and color saturation of the colors of the active portion of the time-temperature indicator, and for comparison of the colors, said comparison using a densitometer-like instrument for measuring optical density of the color saturation.

* * * * *